(12) United States Patent
Alvarez et al.

(10) Patent No.: US 6,559,161 B1
(45) Date of Patent: May 6, 2003

(54) CYTOTOXIC PYRIDO[2,3,4-KI]ACRIDINE DERIVATIVES, THEIR PREPARATION AND THEIR THERAPEUTIC USE

(75) Inventors: Mercedes Alvarez, Barcelona (ES); Lidia Feliu, Barcelona (ES); Dolores Garcia Gravalos, Barcelona (ES); Jose Luis Fernandez-Puentes, Barcelona (ES)

(73) Assignee: Universidad de Barcelona, Barcelona (ES)

(*) Notice: Subject to any disclaimer, the term of this patent is extended or adjusted under 35 U.S.C. 154(b) by 0 days.

(21) Appl. No.: 10/048,340

(22) PCT Filed: Jul. 27, 2000

(86) PCT No.: PCT/GB00/02888

§ 371 (c)(1),
(2), (4) Date: May 9, 2002

(87) PCT Pub. No.: WO01/09133

PCT Pub. Date: Feb. 8, 2001

(65) Prior Publication Data (65)

(30) Foreign Application Priority Data

Jul. 30, 1999 (GB) ............................................. 9918079

(51) Int. Cl.$^7$ ..................... A61K 31/4738; C07D 47/06

(52) U.S. Cl. ........................................ 514/288; 546/66

(58) Field of Search ............................. 514/288; 546/66

(56) References Cited

FOREIGN PATENT DOCUMENTS

| EP | 0331320 A2 | 9/1989 |
|---|---|---|
| WO | WO98/49165 A1 | 11/1998 |

OTHER PUBLICATIONS

Mercedes Alverez et al., "Preparation of New Pyridoaridine Derivatives and Formal Synthesis of 11–Hydroxyascididemine," Tetrahedron (2000), vol. 56, pp. 3703–3708.

Mercedes Alverez et al., "Synthesis of Ascididemine and an Isomer," European Journal of Organic Chemistry (2000), pp. 849–855.

Leonard A. McDonald et al., "Inhibition of Topoisomerase II Catalytic Activity by Pyridoacridine Alkaloids from a Cystodytes sp. Ascidian: A Mechanism for the Apparent Intercalator–Induced Inhibition of Topoisomerase II," Journal of Medicinal Chemistry (1994), vol. 37(22), pp. 3819–3827.

Jinwoong Kim et al., "Pantherinine, a Cytotoxic Aromatic Alkaloid, and 7–Deazainosine From The Ascidian Aplidium Pantherinum," Journal of Natural Products (1993), vol. 56(10), pp. 1813–1816.

Jun'ichi Kobayashi et al., "Cystodytins D–I, New Cytotoxic Tetracyclic Aromatic Alkaloids From The Okinawan Marine Tunicate Cystodytes Dellechiajei," Journal of Natural Products (1991), vol. 54(6), pp. 1634–1638.

Paul W. Groundwater et al., "Heterocycle–Fused Acridines," Advances in Heterocyclic Chemistry, vol. 70, pp. 89–161.

Amira Rudi et al., "Six New Alkaloids from the Purple Red Sea Tunicate Eudistoma sp.," Journal of Organic Chemistry (1989), vol. 54, pp. 5331–5337.

Tadeusz F. Molinski "Marine Pyridoacridine Alkaloids: Structure, Synthesis, and Biological Chemistry," Chemical Reviews (1993), vol. 93, pp. 1825–1838.

Jun'ichi Kobayashi, et al., "Cystodytins A, B, and C, Novel Tetracyclic Aromatic Alkaloids with Potent Antineoplastic Activity from the Okinawan Tunicate Cystodytes Dellechiajei," Journal of Organic Chemistry (1987), vol. 53, pp. 1800–1804.

Philip A. Searle et al., "Five New Alkaloids from the Tropical Ascidian, Lissoclinum sp Lissoclinotoxin A is Chiral," Journal of Organic Chemistry (1994), vol. 59, pp. 6600–6605.

(List continued on next page.)

Primary Examiner—C. S. Aulakh
(74) Attorney, Agent, or Firm—Fish & Richardson P.C.

(57) ABSTRACT

The invention provides compounds of formula (I)

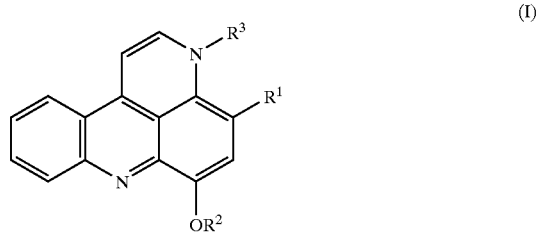

wherein
$R^1$ represents a hydrogen atom, an alkyl group having from 1 to 6 carbon atoms, a hydroxy group, an alkoxy group having from 1 to 6 carbon atoms, a halogen atom, a nitro group, an amino group, a monoalkylamino group wherein the alkyl moiety has from 1 to 6 carbon atoms, a dialkylamino group wherein each alkyl moiety may be the same or different and each has from 1 to 6 carbon atoms, a dialkoxyamino group wherein each alkoxy moiety may be the same or different and each has from 1 to 6 carbon atoms, an alkanoylmino group having from 1 to 20 carbon atoms or an alkanesulfonylamino group having from 1 to 6 carbon atoms;

$R^2$ represents a hydrogen atom or an alkyl group having from 1 to 6 carbon atoms; and $R^3$ represents a hydrogen atom, an alkyl group having from 1 to 6 carbon atoms or an alkoxy group having from 1 to 6 carbon atoms;

and pharmaceutically acceptable salts thereof. The compounds exhibit activity against a wide variety of mammalian cancer cell lines.

16 Claims, No Drawings

OTHER PUBLICATIONS

Mercedes Alverez et al., "Marine, Nitrogen–Containing Heterocyclic Natural Products. Structures and Syntheses of Compounds Containing Quinoline and/or Isoquinoline Units," Heterocycles (1991), vol. 32, pp. 759–794.

Mercedes Alverez et al., "Synthesis of Pyridoacridines," Heterocycles (1992), vol. 34, pp. 2385–2405.

Amira Rudi et al., "Alkaloid Metabolites of the Marine Tunicate Eudistoma sp.: Segoline A, Isosegoline A and Nor–Segoline," Tetrahedron Letters (1988), vol. 29(31), pp. 3861–3862.

Maria Ionescu et al., "Syntehsis of Some Dimethoxy–10–Methylacridones," Revue Roumaine de Chimie (1969), vol. 14, pp. 789–795.

Geeta A. Charyulu et al., "Diplamine, A Cytotoxic Polyaromatic Alkaloid from the Tunicate Diplosoma sp.," Tetrahedron Letters (1989), vol. 30(32), pp. 4201–4202.

Raymond J. Bergeron et al., "Antineoplastic and Antiherpetic Activity of Spermidine Catecholamide Iron Chelators," Biochemical and Biophysical Research Communications (1984), vol. 121(3), pp. 848–854.

Alan C. Schroeder et al., "Synthesis and Biological Effects of Acyclic Pyrimidine Nucleoside Analogues," Journal of Medicinal Chemistry (1981), vol. 24(9), pp. 1078–1083.

Tadeusz F. Molinski et al., "Varamines A and B, New Cytotoxic Thioalkaloids from Lissoclinum vareau," Journal of Organic Chemistry (1989), vol. 54, pp. 4256–4259.

CYTOTOXIC PYRIDO[2,3,4-KI]ACRIDINE DERIVATIVES, THEIR PREPARATION AND THEIR THERAPEUTIC USE

This application is a 371 of PCT/GB00/02888 filed Jul. 27, 2000, now WO 01/09133.

FIELD OF THE INVENTION

This invention relates to novel pyrido[2,3,4-k,l]acridine compounds. The invention also relates to their use in the treatment of cancers and processes for preparing them.

DESCRIPTION OF PRIOR ART

The polycyclic aromatic alkaloids based on the pyrido[2,3,4-k,l]acridine skeleton are a growing class of ascidian metabolites that often exhibit a variety of interesting biological properties, including antitumour activity, as reviewed by Molinksy (1993), Álvarez and Joule (1992), Álvarez et al (1991) and Groundwater and Munawar (1998). As examples of these alkaloids, there are described: norsegoline (Rudi et al, 1988), varamines (Molinsky and Ireland, 1989), Iissoclins (Searle and Molinsky, 1994), diplamine (McDonald et al, 1994; Chryulu and McKee, 1989), isobutyramide (Molinksy, 1993), cystodytins (Kobayashi wt al, 1988 and 1991), and pantherinine (Kim et al, 1993). The structures of these compounds are shown below.

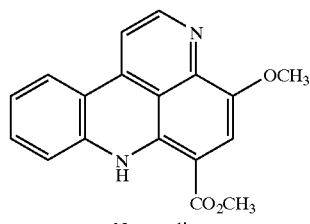
Norsegoline

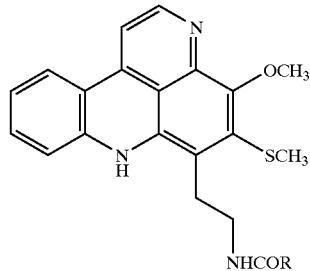
R = Me
R = Et
varamines

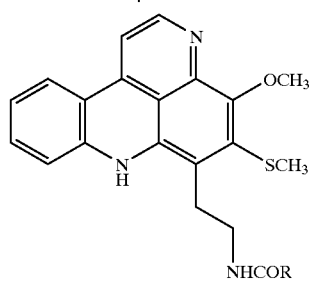
R = Me₂CHCH₂
R = cis-MeCH=CMe
lissoclins
R = Me — diplamine
R = Me₂CH — isobutyramide

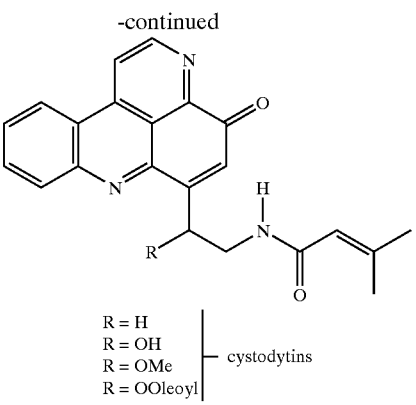
R = H
R = OH
R = OMe
R = OOleoyl
cystodytins

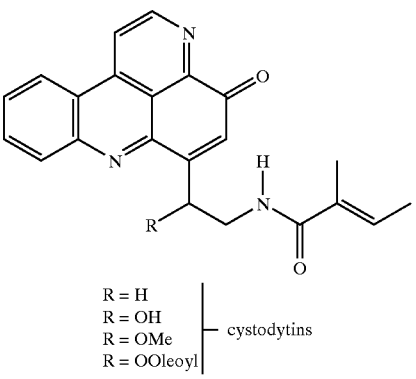
R = H
R = OH
R = OMe
R = OOleoyl
cystodytins

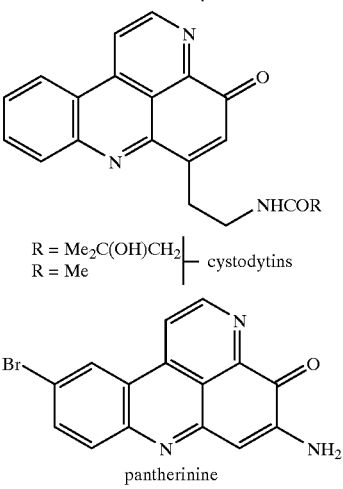
R = Me₂C(OH)CH₂
R = Me
cystodytins pantherinine

Biological studies on pyridoacridines are severely limited due to their very low availability from natural sources, and therefore the study of their mechanism of action and the establishment of reliable structure-activity relationships requires the development of efficient synthetic routes.

SUMMARY OF INVENTION

The present inventors have developed an efficient process for producing compounds containing the pyrido[2,3,4-k,l] acridine skeleton in a small number of steps from commonly available starting materials. Furthermore, the novel compounds produced by the process exhibit activity against a wide variety of mammalian cancer cell lines.

Therefore, in a first aspect, the invention provides compounds of formula (I):

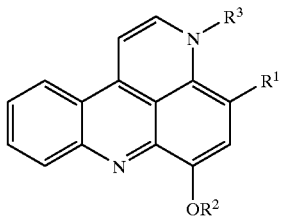

(I)

wherein:
R¹ represents a hydrogen atom, an alkyl group having from 1 to 6 carbon atoms, a hydroxy group, an alkoxy group having from 1 to 6 carbon atoms, a halogen atom, a nitro group, an amino group, a monoalkylamino group wherein the alkyl moiety has from 1 to 6 carbon atoms, a dialkylamino group wherein each alkyl moiety may be the same or different and each has from 1 to 6 carbon atoms, a monoalkoxyamino group wherein the alkoxy moiety has from 1 to 6 carbon atoms, a dialkoxyamino group wherein each alkoxy moiety may be the same or different and each has from 1 to 6 carbon atoms, an alkanoylamino group having from 1 to 20 carbon atoms or an alkanesulfonylamino group having from 1 to 6 carbon atoms;

R² represents a hydrogen atom or an alkyl group having from 1 to 6 carbon atoms; and R³ represents a hydrogen atom, an alkyl group having from 1 to 6 carbon atoms or an alkoxy group having from 1 to 6 carbon atoms;

and pharmaceutically acceptable salts thereof.

In a second aspect, this invention provides a pharmaceutical composition containing as an active ingredient a compound of formula (I) as defined above or a pharmaceutically acceptable salt thereof together with a pharmaceutically acceptable carrier or diluent.

In a third aspect, the invention provides a method for treating a mammal affected by a malignant tumour sensitive to a compound of formula (I) as defined above, which comprises administering to a mammal in need of such treatment a therapeutically effective amount of a compound of formula (I), a pharmaceutically acceptable salt thereof or a pharmaceutical composition thereof as defined above.

In a fourth aspect, the invention provides the use of a compound of formula (I) as defined above, or a pharmaceutically acceptable salt thereof in the manufacture of a medicament for the treatment or prophylaxis of malignant tumours.

In a fifth aspect, the invention provides a method for preparing a compound of formula (I) as defined above or a pharmaceutically acceptable salt thereof, described in more detail hereinafter.

DETAILED DESCRIPTION OF PREFERRED EMBODIMENTS

The compounds of formula (I) above are defined in more detail below.

The alkyl group may be a straight-chain or branched alkyl group having 1 to 6 carbon atoms such as methyl, ethyl, propyl, isopropyl, butyl, isobutyl, sec-butyl, tert-butyl, pentyl, neopentyl and hexyl. Of these groups, alkyl groups having from 1 to 4 carbon atoms are preferred, particularly the methyl and ethyl groups, and the methyl group is especially preferred.

The alkoxy group comprises an oxygen atom substituted by a straight-chain or branched alkyl group having 1 to 6 carbon atoms such as those described and exemplified above. As examples of such groups, there may be mentioned the methyoxy, ethoxy, propoxy, isopropoxy, butoxy, isobutoxy, sec-butoxy, tert-butoxy, pentyloxy and hexyloxy groups. Alkoxy groups having from 1 to 4 carbon atoms are preferred, and the methoxy and ethoxy groups are especially preferred.

The monoalkylamino group comprises an amino group which is substituted by an alkyl group having 1 to 6 carbon atoms such as those described and exemplified above. As examples of such groups there may be mentioned the methylamino, ethylamino, propylamino, isopropylamino, butylamino, pentylamino and hexylamino groups. Monoalkylamino groups wherein the alkyl group has from 1 to 4 carbon atoms are preferred.

The dialkylamino group comprises an amino group which is substituted by two alkyl group having 1 to 6 carbon atoms such as those described and exemplified above. The alkyl groups may be the same or different, but are preferably the same. As examples of such groups there may be mentioned the dimethylamino, diethylamino, N-methylethylamino, diisopropylamino, dibutylamino, dipentylamino and dihexylamino. Dialkylamino groups wherein each alkyl group has from 1 to 4 carbon atoms are preferred.

The monoalkoxyamino group comprises an amino group which is substituted by an alkoxy group having 1 to 6 carbon atoms such as those described and exemplified above. The dialkoxyamino group comprises an amino group which is substituted by two alkoxy group having 1 to 6 carbon atoms such as those described and exemplified above. The alkoxy groups may be the same or different, but are preferably the same.

The alkanoylamino group comprises an amino group which is substituted by an alkanoyl group having from 1 to 20 carbon atoms, examples of which include the formyl, acetyl, propanoyl, butanoyl, pentanoyl, 2,2-dimethylpropanoyl (pivaolyl), hexanoyl, heptanoyl, octanoyl, nonanoyl, decanoyl, dodecanoyl (lauroyl), tetradecanoyl (myristoyl), hexadecanoyl (palmitoyl), octadecanoyl (stearoyl) and icoscanoyl (arachidoyl) groups. Of the alkanoylamino groups, those groups having from 1 to 6 carbon atoms, particularly from 1 to 4 carbon atoms, are preferred, and the formylamino and acetylamino groups are especially preferred.

The alkanesulfonylamino group comprises an amino group which is substituted by an alkanesulfonyl group, of which the alkyl part is a straight-chain or branched alkyl group having 1 to 6 carbon atoms such as those described and exemplified above. Examples of suitable alkanesulfonylamino groups include the methanesulfonylamino, ethanesulfonylamino, propanesulfonylamino, butanesulfonylamino, pentanesulfonylamino and hexanesulfonylamino groups. Of these groups, alkanesulfonylamino groups having from 1 to 4 atoms, especially the methanesulfonylamino and ethanesulfonylamino groups, are preferred.

The compounds of the present invention contain a basic nitrogen atom, and may therefore form salts by addition with an acid. There is no particular restriction on the nature of such salts, provided that, when the salt is used for therapeutic purposes, it must be pharmaceutically acceptable, ie the salt must be about as active, more active, or not unduly less active than the free base compound, and about as toxic, less toxic or not unduly more toxic than the free base compound.

However, when the salt is used for non-therapeutic purposes (eg as an intermediate in the production of further compounds) even this restriction does not apply. Examples of such salts include salts of hydrohalic acids such as hydrofluoric acid, hydrochloric acid, hydrobromic acid and hydroiodic acid; inorganic acid salts such as nitrate, perchlorate, sulfate and phosphate; salts of alkanesulfonic acids such as methanesulfonic acid, trifluoromethanesulfonic acid and ethanesulfonic acid; salts of arylsulfonic acid such as benzenesulfonic acid and p-toluenesulfonic acid; salts of amino acids such as glutamic acid and aspartic acid; and salts of carboxylic acids such as acetic acid, fumaric acid, tartaric acid, oxalic acid, maleic acid, malic acid, succinic acid, benzoic acid, mandelic acid, ascorbic acid, lactic acid, gluconic acid and citric acid.

In one embodiment, the invention provides compounds of formula (I) wherein:

$R^1$ represents a hydrogen atom, an alkyl group having from 1 to 6 carbon atoms, a hydroxy group, an alkoxy group having from 1 to 6 carbon atoms, a halogen atom, a nitro group, an amino group, a monoalkylamino group wherein the alkyl moiety has from 1 to 6 carbon atoms, a dialkylamino group wherein each alkyl moiety may be the same or different and each has from 1 to 6 carbon atoms, a monoalkoxyamino group wherein the alkoxy moiety has from 1 to 6 carbon atoms or a dialkoxyamino group wherein each alkoxy moiety may be the same or different and each as from 1 to 6 carbon atoms, $R^2$ represents a hydrogen atom, an alkyl group having from 1 to 6 carbon atoms or an alkoxy group having from 1 to 6 carbon atoms; and $R^3$ represents a hydrogen atom, an alkyl group having from 1 to 6 carbon atoms or an alkoxy group having from 1 to 6 carbon atoms.

Of the compounds of the present invention, preferred are the compounds of formula (I) and pharmaceutically acceptable salts thereof wherein:

$R^1$ represents a hydrogen atom, an alkyl group having from 1 to 6 carbon atoms, a hydroxy group, an alkoxy group having from 1 to 6 carbon atoms, a nitro group, an amino group, a monoalkylamino group wherein the alkyl moiety has from 1 to 6 carbon atoms, a dialkylamino group wherein each alkyl moiety may be the same or different and each has from 1 to 6 carbon atoms, an alkanoylamino group having from 1 to 20 carbon atoms or an alkanesulfonylamino group having from 1 to 6 carbon atoms;

$R^2$ represents a hydrogen atom or an alkyl group having from 1 to 4 carbon atoms; and $R^3$ represents a hydrogen atom or an alkyl group having from 1 to 4 carbon atoms.

More preferred are the compounds of formula (I) and pharmaceutically acceptable salts thereof wherein:

$R^1$ represents a hydrogen atom, an alkyl group having from 1 to 4 carbon atoms, a nitro group, an amino group, a monoalkylamino group wherein the alkyl moiety has from 1 to 4 carbon atoms, a dialkylamino group wherein each alkyl moiety may be the same or different and each has from 1 to 4 carbon atoms, an alkanoylamino group having from 1 to 6 carbon atoms or an alkanesulfonylamino group having from 1 to 4 carbon atoms;

$R^2$ represents a hydrogen atom or a methyl group; and $R^3$ represents a hydrogen atom or a methyl group.

Even more preferred are the compounds of formula (I) and pharmaceutically acceptable salts thereof wherein:

$R^1$ represents a hydrogen atom, a nitro group, an amino group or an alkanoylamino group having from 1 to 4 carbon atoms;

$R^2$ represents a hydrogen atom or a methyl group; and $R^3$ represents a hydrogen atom.

The following compounds are most preferred:
3H-6-methoxypyrido[2,3,4-kl]acridine;
3H-6-hydroxypyrido[2,3,4kl]acridine;
3H-6-methoxy-4-nitropyrido[2,3,4-kl]acridine;
3H-4-acetylamino-6-methoxypyrido[2,3,4-kl]acridine;
and pharmaceutically acceptable salts thereof.

Examples of pharmaceutical compositions include any solid (tablets, pills, capsules, granules, etc.) or liquid (solutions, suspensions or emulsions) formulations which are suitable for oral, topical or parenteral administration, and they may contain the pure compound or in combination with any carrier or other pharmacologically active compounds. These compositions may need to be sterile when administered parenterally.

The correct dosage of a pharmaceutical composition comprising compounds with formula (I), will vary according to the pharmaceutical formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compounds of formula (I) may be prepared by a number of methods known to those in the art. For example, they may be prepared by reacting a compound of formula (II):

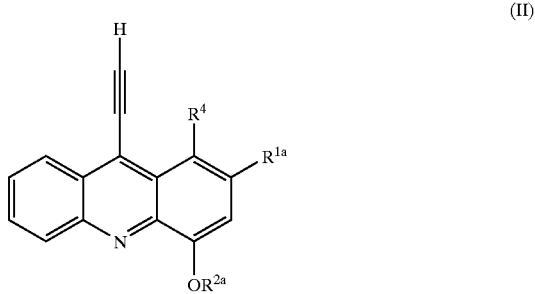

(II)

wherein:

$R^{1a}$ represents any of the groups represented by $R^1$, and any group wherein OH and NH groups (if any) are protected;

$R^{2a}$ represents an alkyl group having from 1 to 6 carbon atoms or a hydroxy-protecting group; and $R^4$ represents a hydrogen atom, an alkyl group having from 1 to 6 carbon atoms or an alkoxy group having from 1 to 6 carbon atoms;

with a compound of formula (III):

$M^{n+}$ [N(CHO)$_2$]$_n$ (III)

wherein M represents a Group 1 metal ion, a Group 2 metal ion or a tetraalkylammonium ion (in which each alkyl group may be the same or different and each has from 1 to 20 carbon atoms), and n stands for an integer equal to the positive valency of M;

to give a compound of formula (Ia):

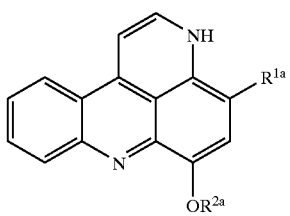

(Ia)

in which $R^{1a}$ and $R^{2a}$ are as defined above;
and, if necessary, removing protecting groups;
and, if necessary, any of the following steps (i) to (v);
 (i) converting the group $R^{1a}$ to any of the other groups represented by $R^1$;
 (ii) where $R^2$ represents an alkyl group, alkylating the product;
 (iii) where $R^3$ represents an alkyl group, alkylating the product;
 (iv) where $R^3$ represents an alkoxy group, alkoxylating the product;
 (v) salifying the product a give a pharmaceutically acceptable salt of the compound of formula (I).

In the compound of formula (II), $R^{1a}$ represents any of the groups represented by $R^1$, and any such group wherein OH and NH groups (if any) are protected, and $R^{2a}$ represents an alkyl group having from 1 to 6 carbon atoms or a hydroxy-protecting group.

The hydroxy-protecting group may be any such group used in the field of organic synthetic chemistry. Suitable protecting groups are described in Greene and Wuts (1991). As non-limiting examples of the hydroxy-protecting group, there may be mentioned the following:
alkanoyl groups having from 1 to 20 carbon atoms such as those defined and exemplified above;
alkanoyl groups having from 1 to 20 carbon atoms which are substituted with a carboxy groups such as succinoyl, glutaroyl and adipoyl groups;
haloalkanoyl groups having from 1 to 20 carbon atoms such as chloroacetyl, dichloroacetyl, trichloroacetyl and trifluoroacetyl groups;
alkanoyl groups having from 2 to 20 carbon atoms which are substituted with one or more alkoxy groups having from 1 to 6 carbon atoms such as methoxyacetyl groups;
aromatic acyl groups wherein the aromatic moiety is a carbocyclic aromatic group having from 6 to 10 ring carbon atoms (which may be further substituted with one or more substituents selected from halogen atoms, alkyl groups having from 1 to 6 carbon atoms, alkoxy groups having from 1 to 6 carbon atoms, carboxy groups, nitro groups and alkoxycarbonyl groups having from 2 to 7 carbon atoms) such as 2-bromobenzoyl, 4-chlorobenzoyl, 2,4,6-trimethylbenzoyl, 4-toluoyl, 4-anisoyl, 2-carboxybenzoyl, 3-carboxybenzoyl 4-carboxybenzoyl, 4-nitrobenzoyl, 2-nitrobenzoyl, 2-(methoxycarbonyl)-benzoyl groups;
tetrahydropyranyl, tetrahydrothiopyranyl, tetrahydrofuranyl or tetrahydrothiofuranyl groups (which may be optionally substituted with one or more substituents selected from halogen atoms, alkyl groups having from 1 to 6 carbon atoms and alkoxy groups having from 1 to 6 carbon atoms) such as tetrahydropyran-2-yl, 3-bromotetrahydropyran-2-yl, 4-methoxytetrahydropyran-4-yl, tetrahydrothipyran-2-yl and 4-methoxytetrahydrothiopyran-4-yl, tetrahydrofuran-2-yl and tetrahydrothiofuran-2-yl groups;
silyl groups, for example, trialkylsilyl groups wherein each alkyl moiety has from 1 to 6 carbon atoms such as trimethylsilyl, triethylsilyl, isopropyldimethylsilyl, t-butyldimethylsilyl, methyldiisopropylsilyl, methyldi-t-butylsilyl and triisopropylsilyl groups and silyl groups substituted with 3 substituents selected from aryl groups (as defined above in relation to aromatic acyl groups) and alkyl groups having from 1 to 6 carbon atoms such as diphenylmethylsilyl, diphenylbutylsilyl, diphenylisopropylsilyl and phenyldiisopropylsilyl groups;
alkoxymethyl groups wherein the alkoxy moiety has from 1 to 6 carbon atoms and may be further substituted with a substituent selected from alkoxy groups having from 1 to 6 carbon atoms and halogen atoms, for example, methoxymethyl, 1,1-dimethyl-1-methoxymethyl, ethoxymethyl, propoxymethyl, isopropoxymethyl, butoxymethyl, t-butoxymethyl, 2-methoxyethoxymethyl and 2,2,2-trichloromethoxymethyl groups;
ethyl groups substituted with a substituent selected from alkoxy groups having from 1 to 6 carbon atoms and halogen atoms, such as 1-ethoxyethyl, 1-(isopropoxy)ethyl and 2,2,2-trichloroethyl groups;
aralkyl groups wherein an alkyl group having from 1 to 6 carbon atoms is substituted with from 1 to 3 aryl groups as defined above in relation to aromatic acyl groups (which may be further substituted with one or more substituents selected from halogen atoms, alkyl groups having from 1 to 6 carbon atoms, alkoxy groups having from 1 to 6 carbon atoms, carboxy groups, nitro groups, cyano groups or alkoxycarbonyl groups having from 2 to 7 carbon atoms) such as benzyl, α-naphthylmethyl, β-naphthylmethyl, diphenylmethyl, triphenylmethyl and α-naphthyldiphenylmethyl groups such as 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, and 4-cyanobenzyldiphenylmethyl groups.

The NH-protecting group may be any such group used in the field of organic synthetic chemistry. Suitable protecting groups are described in Greene and Wuts (1991). As non-limiting examples of the NH-protecting group, there may be mentioned the following:
alkanoyl groups, carboxy-substituted alkanoyl groups, haloalkanoyl groups and alkoxy-substituted alkanoyl groups such as those defined and exemplified above in relation to hydroxy-protecting groups;
aromatic acyl groups wherein the aromatic moiety is a carboxylic aromatic group having from 6 to 10 carbon atoms (which may be further substituted with one or more substituents selected from halogen atoms, alkyl groups having from 1 to 6 carbon atoms, alkoxy groups having from 1 to 6 carbon atoms, cyano groups, carboxy groups, nitro groups, alkoxycarbonyl groups having from 2 to 7 carbon atoms) such as those defined and exemplified above in relation to hydroxy-protecting groups;
silyl groups such as those defined and exemplified above in relation to hydroxy-protecting groups;
aralkyl groups wherein an alkyl group having from 1 to 6 carbon atoms is substituted with from 1 to 3 aryl groups as defined above in relation to aromatic acyl groups (which may be further substituted with one or more substituents selected from halogen atoms, alkyl groups having from 1 to 6 carbon atoms, alkoxy groups having from 1 to 6 carbon atoms, carboxy groups, nitro groups, cyano groups or alkoxycarbonyl groups having from 2 to 7 carbon atoms) such as those defined and exemplified above in relation to hydroxy-protecting groups;

substituted methylene groups, each of which is capable of forming a Schiff base (>C=NH) such as N,N-dimethylaminomethylene, benzylidene, 4-methoxybenzylidene, 4-nitrobenzylidene, salicylidene, 5-chlorosalicylidene, diphenylmethylene and (5-chloro-2-hydroxphenyl)phenylmethylene groups.

The compound of formula (III) is a diformylamide compound, such as lithium diformylamide or sodium diformylamide, of which sodium diformylamide is preferred. The amount of the compound of formula (III) used is generally 1 to 5 molar equivalents, preferably 1.5 to 3 more equivalents, of the compound of formula (II).

The reaction is generally and preferably carried out in the presence of a solvent. There is no particular restriction on the nature of the solvent, provided that it has no adverse effect on the reaction and can dissolve the starting material therein to some extent. As non-limiting examples of the solvent, there may be mentioned aromatic hydrocarbons such as benzene, toluene and xylene; aliphatic hydrocarbons such as pentane, hexane and heptane and mixtures thereof; halogenated hydrocarbons such as dichloromethane, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutyronitrile; amides such as formamide, N,N-dimethylformamide, N,N-dimethylacetamide, N-methyl-2-pyrrolidone and hexamethylphosphoric triamide; and sulfoxides such as dimethylsulfoxide and sulfolane. Of these, amides, especially N,N-dimethylformamide, are preferred.

The reaction temperature ranges from room temperature to 200° C., and is preferably 100° C. to 170° C. In particular, when the solvent is N,N-dimethylformamide, the reaction temperature is most preferably between 140° C. and 160° C.

Although the reaction time varies depending on the reaction temperature, starting materials, reagents and nature of the solvent, it usually ranges from 5 minutes to 3 hours, and is preferably from 10 minutes to 1 hour, more preferably 20 to 40 minutes.

The compound of formula (II) may be prepared by the method described in Scheme 1 below.

Scheme 1

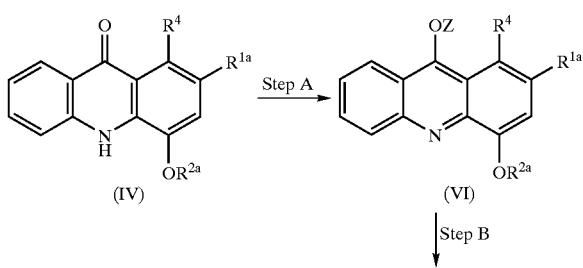

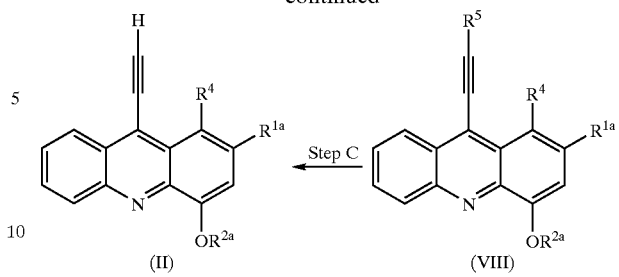

In the above Scheme 1, $R^{1a}$, $R^{2a}$ and $R^4$ are defined above; Z is a group capable of converting a hydroxy group into a leaving group (as defined below), and $R^5$ is a protecting group for an acetylenic hydrogen (as defined below).

Scheme 1 comprises three steps, each of which are described in more detail below.

In Step A, an acridone compound of formula (IV):

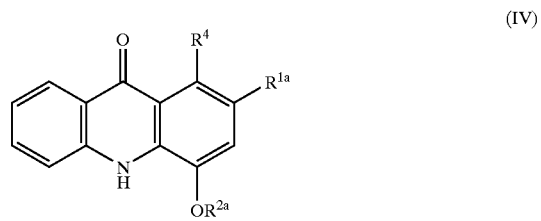

in which $R^{1a}$, $R^{2a}$ and $R^4$ are as defined above, is reacted with a compound of formula (V):

in which:
Z is a group capable of converting a hydroxy group into a leaving group; and
Z' is a leaving group.
to give a compound of formula (VI):

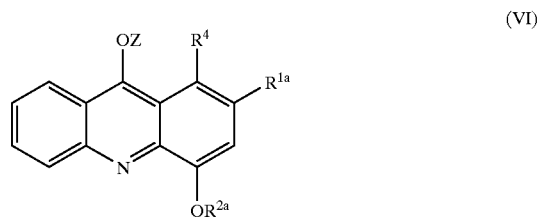

in which $R^{1a}$, $R^{2a}$ and $R^4$ are as defined above.

Compounds of formula (IV) are known in the art. For example, the compound of formula (IV) wherein $R^{2a}$ is a methyl group and $R^4$ is a methoxy group is described in Ionescu and Mester (1969).

In the compounds of formula (V), Z is a group capable of converting a hydroxy group into a leaving group. Any group known in the art to be capable of converting a hydroxy group into a leaving group may be suitable. As non-limiting examples of the group Z, there may be mentioned alkanoyl groups having from 1 to 20 carbon atoms such as those defined and exemplified above in relation to alkanoylamino groups, alkanesulfonyl groups having from 1 to 6 carbon atoms such as those defined and exemplified above in relation to alkanesulfonylamino groups, arylsulfonyl groups such as the benzenesulfonyl group and the p-toluenesulfonyl group, and haloalkanesulfonyl groups wherein an alkanesulfonyl group having from 1 to 6 carbon atoms such as those defined and exemplified above in relation to alkanesulfonylamino groups is substituted in one or more (preferably all) substitutable positions by a halogen atom, such as the trifluoromethanesulfonyl group and the perfluorobutanesulfonyl group. Of these, the trifluoromethanesulfonyl group is especially preferred.

The group Z' is a leaving group, and any leaving group known in the art may be suitable. As non-limiting examples of the group Z', there may be mentioned halogen atoms such as chlorine, bromine and iodine, alkanoate groups wherein the alkanoyl part has from 1 to 20 carbon atoms such as those defined and exemplified above in relation to alkanoylamino groups, alkanesulfonate groups having from 1 to 6 carbon atoms wherein the alkanesulfonyl part is defined and exemplified above in relation to alkanesulfonylamino groups, arylsulfonate groups such as the benzenesulfonate and the p-toluenesulfonate group, or haloalkanesulfonate groups wherein the haloalkanesulfonyl moiety is defined and exemplified above, such as the trifluoromethanesulfonate ion and the perfluorobutane-sulfonate ion, of which the trifluoromethanesulfonate ion is preferred.

The reaction is generally and preferably carried out in the presence of a solvent. There is no particular restriction on the nature of the solvent, provided that is has no adverse effect on the reaction and can dissolve the starting material therein to some extent. As non-limiting examples of the solvent, there may be mentioned aromatic hydrocarbons such as benzene, toluene and xylene; aliphatic hydrocarbons such as pentane, hexane and heptane and mixtures thereof; halogenated hydrocarbons such as dichloromethane, chloroform, carbon tetrachloride, dichloromethane, chlorobenzene and dichloromethane; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutyronitrile; amides such as formamide, N,N-dimethylformamide, N,N-dimethylacetamide, N-methyl-2-pyrrolidone and hexamethylphosphoric triamide; and sulfoxides such as dimethylsulfoxide and sulfolane. Of these, halogenated hydrocarbons, especially dichloromethane, are preferred.

The amount of the compound of formula (V) used is generally 1 to 5 molar equivalents, preferably 1.1 to 2 molar equivalents, of the compound of formula (IV).

The reaction is generally carried out in the presence of a base, and similarly there is no particular restriction on the nature of the base, provided it is capable of acting as a base (in particular, to neutralise any acidic by-product formed in the reaction). However, weak bases, ie those for which $pK_a$ of the conjugate acid is greater than 0 (those which would not fully ionise in solution) are preferred. As non-limiting examples of the base there may be mentioned alkali metal carbonates and hydrogencarbonates such as sodium carbonate, potassium carbonate and sodium hydrogencarbonate, aliphatic and heterocyclic amines such as trimethylamine, triethylamine, N,N-diisopropylethylamine, tributylamine, pyrrolidine, piperidine and 1,8-diazabicyclo[5.4.0]-7-undecene, and aromatic and heteroaromatic amines such as pyridine, 2,6-dimethylpyridine (2,6-lutidine) and 4-(N,N-dimethylamino) pyridine (DMAP), of which the heteroaromatic amines are preferred. The amount of base used is generally 1 to 5 molar equivalents, preferably 1.1 to 3 molar equivalents, of the compound of formula (IV).

The reaction may be carried out in the presence of a catalyst, particularly a nucleophilic catalyst. Although any suitable catalyst may be used, 4-(N,N-dimethylamino) pyridine (DMAP) is preferred. The amount of catalyst used is generally 0.05 to 0.5 molar equivalents, preferably 0.1 to 0.3 molar equivalents, of the compound of formula (IV).

The reaction temperature ranges from −20° C. to 100° C., preferably 0° C. to 50° C.

Although the reaction time varies depending on the reaction temperature, starting material compounds, reagents and nature of the solvent, it usually ranges from 10 minutes to 3 days, preferably from 30 minutes to 12 hours.

In Step B, the compound of formula (VI) defined above is reacted with a compound of formula (VII):

H—C≡C—R⁵ (VII)

in which $R^5$ is a protecting group for an acetylenic hydrogen, to give a compound of formula (VIII):

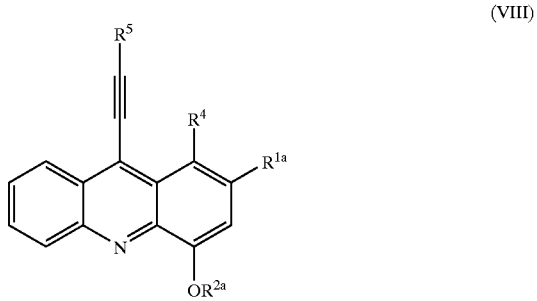

(VIII)

in which $R^1$, $R^{2a}$, $R^4$ and $R^5$ are as defined above.

In the compounds of formula (VII), the group $R^5$ is a protecting group for an acetylenic hydrogen. Any group known in the art to be suitable for protecting an acetylenic hydrogen may be used. However, silyl groups such as those defined and exemplified above in relation to hydroxy-protecting groups are preferred and the trimethysilyl group is especially preferred.

The amount of the compound of formula (VII) used is generally 1 to 10 molar equivalents, preferably 2 to 5 molar equivalents, of the compound of formula (VI).

The reaction is generally and preferably carried out in the presence of a solvent. There is no particular restriction on the nature of the solvent, provided that is has no adverse effect on the reaction and can dissolve the starting material therein to some extent. As non-limiting examples of the solvent, there may be mentioned aromatic hydrocarbons such as benzene, toluene and xylene; aliphatic hydrocarbons such as pentane, hexane and heptane and mixtures thereof; halogenated hydrocarbons such as dichloromethane, chloroform, carbon tetrachloride, dichloromethane, chlorobenzene and dichloromethane; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutyronitrile; amides such as formamide, N,N-dimethylformamide, N,N-dimethylacetamide, N-methyl-2-pyrrolidone and hexamethylphosphoric triamide; and sulfoxides such as dimethylsulfoxide and sulfolane. Of these, ethers, especially tetrahydrofuran, are preferred.

The reaction is generally carried out in the presence of a base, and similarly there is no particular restriction on the nature of the base, provided it is capable of acting as a base (in particular, to neutralise any acidic by-product formed in the reaction). However, weak bases (as defined above) are preferred. As non-limiting examples of the base there may be mentioned alkali metal carbonates and hydrogencarbonates such as sodium carbonate, potassium carbonate and sodium hydrogencarbonate, aliphatic and heterocyclic amines such as trimethylamine, triethylamine, N,N-diisopropylamine, tributylamine, pyrrolidine, piperidine and 1,8-diazabicyclo[5.4.0]-7-undecene, and aromatic and heteroaromatic amines such as pyridine, 2,6-dimethylpyridine (2,6-lutidine) and 4-(N,N-dimethylamino)pyridine (DMAP), of which aliphatic amines, especially N,N-diisopropylethylamine, are preferred. The amount of base used is generally 1 to 10 molar equivalents, preferably 2 to 6 molar equivalents, of the compound of formula (VI).

The reaction is preferably carried out in the presence of a catalyst, and any substance capable of catalysing the reaction may be used. However, palladium compounds, especially tetrakis(triphenylphosphine)palladium (0), are preferred. The amount of catalyst used is generally 0.001 to 0.5 molar equivalents, preferably 0.01 to 0.2 molar equivalents, of the compound of formula (VI).

The reaction temperature ranges from room temperature to 100° C., and is preferably 50° C. to 80° C. In particular, when the solvent is tetrahydrofuran, the reaction temperature is between 65° C. and 70° C.

Although the reaction time varies depending on the reaction temperature, starting material compounds, reagents and nature of the solvent, it usually ranges from 10 minutes to 3 days, and is preferably from 30 minutes to 12 hours, more preferably 2 hours to 8 hours.

In Step C, the protecting group $R^5$ of the compound of formula (VIII) is removed to produce a compound of formula (II).

The nature of the reagent used depends on the nature of the protecting group $R^5$ to be removed. However, when the protecting group $R^5$ is a silyl group, the group may be removed under acidic conditions (for example, but not limited to acetic acid, or hydrochloric acid or citric acid), basic conditions (for example, but not limited to potassium carbonate), or using a source of fluoride ion (for example, but not limited to tetrabutylammonium fluoride, sodium fluoride, potassium fluoride, hydrofluoric acid, HF-pyridine, HF-triethylamine). Removal of the protecting group using a source of fluoride ion is preferred and the use of potassium fluoride or tetrabutylammonium fluoride is especially preferred.

The amount of the reagent used to remove the protecting group $R^5$ depends on the nature of the protecting group $R^5$ to be removed. However, when the protecting group $R^5$ is a silyl group, the amount of the reagent used is generally 1 to 10 molar equivalents, preferably 2 to 5 molar equivalents, of the compound of formula (VII).

The reaction is generally and preferably carried out in the presence of a solvent. There is no particular restriction on the nature of the solvent, provided that it has no adverse effect on the reaction and can dissolve the starting material therein to some extent. As non-limiting examples of the solvent, there may be mentioned water, alcohols such as methanol, ethanol, isopropanol and t-butanol, aromatic hydrocarbons such as benzene, toluene and xylene; aliphatic hydrocarbons such as pentane, hexane and heptane and mixtures thereof; halogenated hydrocarbons such as dichloromethane, chloroform, carbon tetrachloride, dichloroethane, chlorobenzene and dichlorobenzene; esters such as ethyl formate, ethyl acetate, propyl acetate, butyl acetate and diethyl carbonate; ethers such as diethyl ether, diisopropyl ether, tetrahydrofuran, dioxane, dimethoxyethane and diethylene glycol dimethyl ether; nitriles such as acetonitrile and isobutyronitrile; amides such as formamide, N,N-dimethylformamide, N,N-dimethylacetamide, N-methyl-2-pyrrolidone and hexamethylphosphoric triamide; and sulfoxides such as dimethylsulfoxide and sulfolane. Of these, alcohols, especially methanol, and ethers, especially tetrahydrofuran, are preferred.

The compound of formula (II) may then be reacted with a compound of formula (III) to produce a compound of formula (I) as described above. Further compounds of formula (I) may be prepared be derivatising another compound of formula (I).

Preparation of the compounds of the invention are described in the Examples below.

Preparation of the starting materials is described in the Preparations.

EXAMPLES

General Experimental Details

Melting points were determined in a capillary tube and are uncorrected. TLC was carried out on $SiO_2$ (silica gel 60 $F_{254}$, Merck 0.063–0.200 mm) and spots were located with UV light. Column chromatography was carried out on $SiO_2$ (silica gel 60 SDS 0.060–0.2 mm). Flash chromatography was carried out on $SiO_2$ (silica gel 60 A CC, Merck). Organic extracts were dried with anhydrous $Na_2SO_4$, and solutions were evaporated under reduced pressure with a rotary evaporator. Infra-red (IR) spectra were performed with a Nicolet 205 FT-IR; data are given in wavenumbers (v) in $cm^{-1}$ using the following abbreviations: s: strong; m, medium; w, weak. Nuclear magnetic resonance (NMR) spectra were measured with Varian Gemini-200 (200 MHz), Varian Gemini-300 (300 MHz) and Varian VXR-500 (500 MHz) spectrometers; chemical shift data (δ) are given in parts per million (ppm) referenced to tetramethylsilane and using the following abbreviations: s, singlet; d, doublet; t, triplet; q, quartet. For the compounds of Examples 1 to 4, the carbons are numbered as outlined in the skeleton structure below. Mass spectra were measured in the electron impact (EI) or chemical ionization (CI) mode with a Hewlett-Packard model 5989A. High resolution mass spectra were performed with an Autospec/VG by the Department de Química Orgànica Biològica (CSIC) Barcelona. Elemental analyses were performed with a C E Instruments EA-1108 in the Serveis Científico-Tècnics de la Universitad de Barcelona.

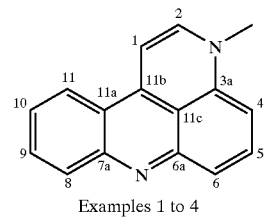

Examples 1 to 4

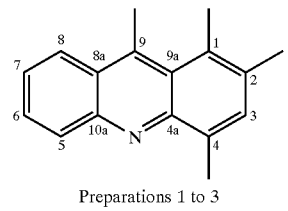

Preparations 1 to 3

Example 1

3H-6-Methoxypyrido[2,3,4-kl]acridine

Sodium diformylamide (190 mg, 2.0 mmol) was added to a solution of 1,4-dimethoxy-9-ethynylacridine (prepared as described in Preparation 3 below) (217 mg, 0.8 mmol) in dry DMF (2 ml) and the mixture was stirred at reflux for 30 min. The solvent was removed and the residue was dissolved in $CH_2Cl_2$ and washed with $H_2O$. The organic solution was dried and evaporated affording a residue which was purified by column chromatography. Elution with $CH_2Cl_2$/MeOH (99:2) gave the title compound (109.5 mg, 55%); m.p. 148–150° C. (EtOAc). IR (KBr): $v/cm^{-1}$=1686 (s, C≡N), 1599 (s, Ar), 1573 (s, Ar), 1460 (s, Ar); $^1$H NMR (500 MHz, $CDCl_3$): $\delta_H$/ppm=3.85 (s, 3H, $OCH_3$), 6.75 (d, J=7.8 Hz, 1H, H-8), 6.85 (dd, J=8.0 and 7.5 Hz, 1H-10), 6.99 (d, J=5.0 Hz, 1H, H-1), 7.18 (dd, J=7.8 and 7.5 Hz, 1H, H-9), 7.20 (d, J=9.0 Hz, 1H, H-4), 7.23 (d, J=9.0 Hz, 1H, H-5), 7.66 (d, J=8.0 Hz, 1H, H-11), 8.37 (d, J=5.0 Hz, 1H, H-2); $^{13}$C NMR (50.3 MHz, $CDCl_3$): $\delta_C$/ppm=56.3 (q, $OCH_3$), 106.1 (d, C-1), 115.1 (d, C-4), 115.3 (d, C-5), 115.6 (d, C-8), 117.4 (s, C-11a), 118.7 (s, C-11c), 121.0 (d, C-10), 123.9 (d, C-11), 125.2 (s, C-6), 131.5 (d, C-9), 137.2 (s, C-6a), 139.2 (2s, C-7a and C-11b), 144.5 (s, C-3a), 150.3 (d, C-2); MS (EI); m/z (%)=249 [M+1] (11), 248 [M$^+$] (45), 234 (21), 233 (100); HRMS: calcd, for $C_{16}H_{12}N_2O$ 248.0949; found 248.0938; Elemental analysis: $C_{16}H_{12}N_2O.0.5CH_3CO_2C_2H_5$ (292.35): calcd. C 73.95, H 5.52, N 9.58; found C 73.67, H 5.42, N, 9.64.

Example 2

3H-6-Hydroxypyrido[2,3,4-kl]acridine

Boron tribromide (8.3 ml, 8.3 mmol) was added to a solution of 3H-6-methoxypyrido[2,3,4-kl]acridine (prepared as described in Example 1 above) (0.4 g, 1.6 mmol) in $CH_2Cl_2$ (20 mil) cooled at −78° C. and maintained under nitrogen. The reaction temperature was increased gradually to −30° C. during 90 min and then to room temperature during 30 min. The reaction mixture was neutralised with saturated aq. $Na_2CO_3$ and extracted with $CH_2Cl_2$. The organic solution was dried and evaporated to give the title compound as a gum. IR (KBr): $v/cm^{-1}$=3440 (s, OH and NH), 1588 (s, Ar), 1318 (s, Ar), 1052 (s, Ar); $^1$H NMR (300 MHz, $CD_3OD$): $\delta_H$/ppm=6.92 (d, J=8.7 Hz, 1H, H-4), 7.04 (d, J=6.5 Hz, 1H, H-1), 7.09 (dd, J=8.5 and 7.1 Hz, 1H, H-10), 7.28 (d, J=8.4 Hz, 1H, H-8), 7.33 (d, J=8.7 Hz, 1H, H-5), 7.51 (dd, J=8.4 and 7.1 Hz, 1H, H-9), 7.79 (d, J=8.5 Hz, 1H, H-11), 7.93 (d, J=6.5 Hz, 1H, H-2); $^{13}$C NMR (75.4 MHz, $CD_3OD$): $\delta_C$/ppm=104.1 (d, C-1), 106.1 (d, C-4), 116.3 (s, C-11a), 118.6 (d, C-5), 121.1 (s, C-6b), 121.6 (d, C-8), 124.0 (d, C-10), 126.1 (d, C-11), 127.0 (s, C-11b), 132.9 (s, C-7a), 136.1 (d, C-9), 139.5 (s, C-6a), 141.8 (s, C-3a), 143.2 (d, C-2), 150.3 (s, C-6); MS (EI); m/z (%)=235 [M+1] (26) [M$^+$] (100), 205 (27), 117 (17); HRMS: calcd. for $C_{15}H_{10}N_2O$ 234.0793; found 234.0790.

Example 3

6-Methoxy-4-nitro-3H-pyrido[2,3,4-kl]acridine

A solution of $Cu(NO_3)_2$ (144 mg, 0.6 mmol) in $Ac_2O$ (6 ml) was added to a solution of 3H-6-methoxypyrido[2,3,4-kl]acridine (prepared as described in Example 1 above) (100 mg, 0.4 mmol) in $Ac_2O$ (3 ml) cooled at 0° C. and the mixture was stirred for 3 h at the same temperature. Aqueous NaOH (50%) was added until basic and the mixture was extracted with $CH_2Cl_2$. The organic solution was dried and evaporated to give a crude product which was purified by column chromatography. Elution with $CH_2Cl_2$:MeOH (99:1) affords the title compound (60 mg, 51%), m.p. 220–223° C. ($CH_2Cl_2$). IR (KBr): $v/cm^{-1}$=3390, 1609, 1578, 1263; $^1$H-NMR (500 MHz, $CDCl_3$): $\delta_H$/ppm=4.12 (s, 3H, $OCH_3$), 5.40 (s, 1H, H-5), 7.83 (ddd, J=7.7, 7.5 and 0.5 Hz, 1H, H-10), 7.92 (ddd, J=7.7, 7.5 and 0.5 Hz, 1H, H-9), 8.40 (dd, J=7.7 and 0.5 Hz, 1H, H-8), 8.51 (d, J=5.5 Hz, 1H, H-1), 8.56 (dd, J=7.7 and 0.5 Hz, 1H, H-11), 9.19 (d, J=5.5 Hz, 1H, H-2), $^{13}$C-NMR (75.4 MHz, $CDCl_3$): 67 $_C$/ppm= 57.0 (q, $OCH_3$), 108.1 (d, C-5), 118.5 (s, C-11c), 118.8 (d, C-1), 122.3 (s, C-11a), 122.9 (d, C-11), 130.0 (d, C-10), 131.7 (d, C-9), 132.0 (d, C-8), 137.1 (s, C-11b), 145.1 (s, C-7a), 146.6 (s, C-3a), 149.8 (d, C-2), 164.4 (s, C-6), 183.3 (s, C-6a), MS (EI): m/z (%)=293 [M$^+$] (4), 262 (42), 233 (52), 205 (100); HRMS calculated for $C_{16}H_{11}N_3O_3$ 293.0800; found 293.0798.

Example 4

4-Acetylamino-6-methoxy-3H-pyrido[2,3,4-kl] acridine

A solution of 6-methoxy-4-nitro-3H-pyrido[2,3,4-kl] acridine (prepared as described in Example 3 above) (136 mg, 0.5 mmol) and $SnCl_2$ (0.5 g, 2.0 mmol) in MeOH (5 ml) was refluxed for 2 h. The solvent was evaporated under vacuum, the residue was dissolved in $Ac_2O$ (10 ml) and the resulting solution was refluxed for 30 min. The excess of $Ac_2O$ was evaporated under vacuum, the residue was dissolved in $CH_2Cl_2$ and the organic solution was washed with saturated $NaHCO_3$. The organic layer was dried and evaporated giving the title compound (78 mg, 55%), m.p. 128–132° C. ($CH_2Cl_2$). IR (KBr): $v/cm^{-1}$=2939, 1600, 1461, 1365, 1205; $^1$H-NMR (200 MHz, $CDCl_3$): $\delta_H$/ppm= 3.95 (s, 3H, $OCH_3$), 6.91 (dd, J=8.6 and 1.0 Hz, 1H, H-8), 7.00 (ddd, J=8.2, 7.6 and 1.0 Hz, 1H, H-10), 7.09 (d, J=5.1 Hz, 1H, H-1), 7.18 (s, 1H, H-5), 7.34 (ddd, J=8.6, 7.6 and 1.4 Hz, 1H, H-9); 7.76 (dd, J=8.2 and 1.4 Hz, 1H, H-11); 8.48 (d, J=5.1 Hz, 1H, H-2); $^{13}$C-NMR ($CDCl_3$, 75.4 MHz); $\delta_C$/ppm=56.4 (q, $OCH_3$), 106.5 (d, C-5), 109.1 (d, C-1), 115.8 (d, C-8), 121.2 (d, C-10), 123.8 (d, C-11), 131.7 (d, C-9), 150.4 (d, C-2), 170.2 (s, C=O); MS (EI): m/z (%)= 306 [M+1] (15); 305 [M$^+$] (1); 249 (100); HRMS calculated for $C_{18}H_{16}N_3O_2$ 306.1242; found 306.1255.

Preparation 1

1,4-Dimethoxy-9-trifluoromethylsulfonyloxyacridine

To a solution of 1,4-dimethoxyacridine (prepared as described in Ionescu and Mester (1969)) (1.0 g, 3.9 mmol) in dry $CH_2Cl_2$ (18 ml) under $N_2$ were successively added DMAP (95 mg, 0.8 mmol), 2,6-lutidine (0.6 ml, 55 mmol) and trifluoromethane-sulfonic anhydride (0.8 ml, 4.7 mmol) and the reaction mixture was stirred at 0° C. for 2 h and then for 1 h at rt. The solution was washed with $H_2O$, dried and evaporated. The residue was purified by column chromatography when elution with hexane/$CH_2Cl_2$ (1:1) to give the title compound (1.3 g, 87%), as a yellow solid. IR (KBr): $v/cm^{-1}$=1253 (s, SO), 1030 (s, SO); $^1$H NMR (200 MHz, $CDCl_3$): $\delta_H$/ppm=4.04 (s, 3H, $OCH_3$), 4.14 (s, 3H, $OCH_3$), 6.83 (d, J=8.4 Hz, 1H, H-2), 7.01 (d, J=8.4 Hz, 1H, H-3), 7.68 (dd, J=8.5 and 7.8 Hz, 1H, H-7), 7.86 (dd, J=8.5 and 7.8 Hz, 1H, H-6), 8.22 (d, J=8.5 Hz, 1H, H-5), 8.43 (d, J=8.5 Hz, 1H, H-8); $^{13}$C NMR (50.3 MHz, $CDCl_3$): $\delta_C$/ppm=55.2 (q, $OCH_3$) 56.3 (q, $OCH_3$), 104.2 (d, C-2), 106.6 (d, C-3), 113.3 (s, C-9a), 118.5 (q, $CF_3$), 119.1 (s, C-8a), 120.7 (d, C-7), 122.5 (s, C-4a), 127.6 (d, C-6), 129.8 (d, C-8), 130.9 (d, C-5), 144.2 (s, C-10a), 147.2 (s, C-1), 148.7 (s, C-4), 148.8 (s, C-9); MS (EI); m/z (%)=388 [M+1] (9), 387 [M+] (42), 254 (100), 226 (69); HRMS: calcd. for $C_{16}H_{12}F_3NO_5S$ 387.0388; found 387.0394.

Preparation 2

1,4-Dimethoxy-9-trimethylsilylethynylacridine

To a solution of 1,4-dimethoxy-9-trifluoromethylsulfonyloxyacridine (prepared as described in Preparation 1 above) (1.2 g, 3.1 mmol) in dry tetrahydrofuran (10 ml) under $N_2$ were successively added tetrakis(triphenylphosphine) palladium (0), (0.3 g, 0.3 mmol), N,N-diisopropylethylamine (1.6 ml, 9.3 mmol) and trimethylsilylacetylene (1.3 ml, 9.3 mmol). The mixture was stirred at reflux for 5 h. After this time the solvent was evaporated and the residue was dissolved in $CH_2Cl_2$ and washed with water. The organic solution was dried an evaporated affording a residue which was purified by column chromatography. Elution with hexane/$CH_2Cl_2$ (1:1) gave the title compound (1.0 g, 98%) as a red solid; m.p. 110–111° C. ($CH_2Cl_2$). IR (film): $v/cm^{-1}$=2810 (w, C≡C), 1608 (s, Ar), 1527 (m, Ar), 1468 (s, Ar); $^1$H NMR (200 MHz, $CDCl_3$): $\delta_H$/ppm=0.41 (s, 9H, 3×$CH_3$), 3.99 (s, 3H, $OCH_3$), 4.11 (s, 3H, $OCH_3$), 6.75 (d, J=8.4 Hz, 1H, H-2), 6.93 (d, J=8.4 Hz, 1H, H-3), 7.63 (dd, J=8.0 and 7.2 Hz, 1H, H-7), 7.78 (dd, J=8.4 and 7.2 Hz, 1H, H-6), 8.35 (d, J=8.4 Hz, 1H, H-5), 8.64 (d, J=8.0 Hz, 1H, H-8); $^{13}$C NMR (50.3 MHz, $CDCl_3$): $\delta_C$=0.0 (q, $CH_3$), 55.8 (q, $OCH_3$), 56.1 (q, $OCH_3$), 101.5 (s, ≡C—Si), 103.9 (d, C-2), 105.7 (d, C-3), 111.8 (s, ≡C), 120.5 (s, C-9a), 126.4 (d, C-7), 126.9 (d, C-6), 127.5 (s, C-9), 129.9 (d, C-5), 130.0 (s, C-8a), 130.3 (d, C-8), 142.1 (s, C-4a), 147.0 (s, C-1), 149.4 (s, C-4 and C-10a); MS (EI); m/z (%)=336 [M+1] (10), 335 [M$^+$] (36), 320 (100), 306 (13), 290 (10), 262 (14); HRMS: calcd. for $C_{20}H_{21}NO_2Si$ 335.1341; found 335.1336; Elemental analysis: $C_{20}H_{21}NO_2Si.0.125CH_2Cl_2$ (346.10): calcd. C 69.84, H, 6.19, N, 4.05; found C 69.70, H 6.42, N 4.09.

Preparation 3

1,4-Dimethoxy-9-ethynylacridine

Potassium fluoride (0.5 g, 9.0 mmol) was added to a solution of 1,4-dimethoxy-9-trimethylsilylethynylacridine (prepared as described in Preparation 2 above) (1 g, 3.0 mmol) in methanol (30 ml) and the mixture was stirred at reflux for 30 min. The solvent was evaporated and the residue was dissolved in $CH_2Cl_2$. The organic solution was washed with $H_2O$, dried and evaporated to give the title compound (764 mg, 97%) as a brown solid; m.p. 155–157° C. ($Et_2O$). IR (KBr): $v/cm^{-1}$=2100 (w, C≡C), 1625 (m, Ar), 1460 (m, Ar); $^1$H NMR (200 MHz, $CDCl_3$): $\delta_H$/ppm=3.98 (s, 3H, $OCH_3$), 4.10 (s, 3H, $OCH_3$), 4.20 (s, 1H, ≡CH), 6.75 (d, J=8.4 Hz, 1H, H-2), 6.92 (d, J=8.4 Hz, 1H, H-3), 7.62 (dd, J=8.4 and 7.4 Hz, 1H, H-7), 7.78 (dd, J=8.6 and 7.4 Hz, 1H, H-6), 8.36 (d, J=8.6 Hz, 1H, H-5), 8.66 (d, J=8.4 Hz, 1H, H-8); $^{13}$C NMR (75.4 MHz, $CDCl_3$): $\delta_C$/ppm=56.0 (q, $OCH_3$), 56.1 (q, $OCH_3$), 85.6 (s, ≡C), 92.7 (d, ≡C), 104.1 (d, C-2), 105.8 (d, C-3), 121.0 (s, C-9a), 124.2 (s, C-9), 126.2 (d, C-6), 127.1 (d, C-7), 127.8 (s, C-8a), 130.0 (d, C-8), 130.4 (d, C-5), 141.3 (s, C-4a), 147.5 (s, C-1), 149.3 (s, C-10a), 149.5 (s, C-4); MS (EI); m/z (%)=264 [M+1] (7), 263 [M$^+$] (35), 248 (100); HRMS: calcd. for $C_{17}H_{13}NO_2$ 263.0946; found 263.0940.

BIOLOGICAL ACTIVITY

The compounds of the present invention exhibit antitumour activity against cell lines derived from human solid tumours, such as human lung carcinoma, human colon carcinoma and human melanoma, and, the like, they are active against other tumour cell lines, like leukemia and lymphoma.

The antitumour activity of the compounds of the present invention has been detected in vitro by culturing the tumour cells following the methodology described in Bergeron et al (1984), and by Schroeder et al (1981). Activity against different tumours as mouse lymphoma, human NSC lung carcinoma, human melanoma and human colon carcinoma has been observed.

Some tumours were more sensitive than others. As for example it was found that NSC lung carcinoma and melanoma cells were 100 times more sensitive than mouse lymphoma and 1000 times more sensitive than human colon carcinoma cells.

Example

Biological activity: cells were maintained in logarithmic phase of growth in Eagle's Minimum Essential Medium, with Earle's Balanced Salts, with 2.0 mM L-glutamine, with non-essential amino acids, without sodium bicarbonate (EMEM/neaa); supplemented with 10% Fetal Calf Serium (FCS), $10^{-2}$ M sodium bicarbonate and 0.1 g/l penicillin-G+streptomycin sulfate.

The tumour cell lines employed have been P-388$D_1$ (ATCC CCL-46, suspension culture of a lymphoid neoplasm from DBA/2 mouse), A549 (ATCC CCL-185, monolayer culture of a human lung carcinoma), HT-29 (ATCC HTB-38, monolayer culture of a human colon carcinoma) and SK-MEL-28 (ATCC HTB-72, monolayer culture of a human melanoma).

P-388$D_1$ cells were seeded into 16 mm wells at 1×10$^4$ cells per well in 1 ml aliquots of MEM 5FCS containing the indicated concentration of drug. A separate set of cultures without drug was seeded as control growth to ensure that cells remained in expotential phase of growth. All determinations were carried out in duplicate. After three days of incubation at 37° C., 10% $CO_2$ in a 98% humid atmosphere, an approximate $IC_{50}$ was determined by comparing the growth in wells with drug to the growth in wells control.

A549, HT-29 and SK-MEL-28 were seeded into 16 mm wells at 2×10$^4$ cells per well in 1 ml aliquots of MEM 10FCS containing the indicated concentration of drug. A separate set of cultures without drug and was seeded as control growth to ensure that cells remained in exponential phase of growth. All determinations were carried out in duplicate. After three days of incubation at 37° C., 10% $CO_2$ in a 98% humid atmosphere, the wells were stained with 0.1% Crystal Violet. An approximate $IC_{50}$ was determined by comparing the growth in wells with drug to the growth in wells control.

In Table 1 are presented the cytoxicity expressed as $IC_{50}$ ($\mu$M)

TABLE 1

| | $IC_{50}$ ($\mu$M) | | | |
| --- | --- | --- | --- | --- |
| COMPOUND | P-388$D_1$ ATCC CCL-46 | A549 ATCC- CCL-L-185 | HT-29 ATCC HTB-38 | SK-MEL-28 ATCC HTB-72 |
| Example 1 | 0.50 | 0.05 | 0.50 | 0.05 |
| Example 3 | 0.34 | 0.03 | 0.34 | 0.03 |
| Example 4 | 1.64 | 0.03 | 1.64 | 0.03 |

REFERENCES

The following articles have been cited herein, and they are incorporated herein by reference:

T. F. Molinsky, *Chem. Rev.* 1993, 93, 1825.

M. Álvarez, J. A. Joule, *Heterocycles*, 1992, 34, 2385.

M. Álvarez, M. Salas, J. A. Joule, *Heterocycles*, 1991, 32, 759.

P. W. Groundwater, M. A. Munawar *Adv. Het. Chem.* 1998, 70, 89.

A. Rudi, Y. Benayahu, I. Goldbery, Y. Kashman *Tetrahedron Lett.* 1988, 29, 3861.

A. Rudi, Y. Benayahu, Y. Kashman *J. Org. Chem.* 1989, 54, 5331.
T. F. Molinsky, C. M. Ireland *J. Org. Chem.* 1989, 54, 4256.
P. A. Searle, T. F. Molinsky *J. Org. Chem.* 1994, 59, 6600.
L. A. McDonald, G. S. Eldredge, L. R. Barrows, C. M. Ireland *J. Med. Chem.* 1994, 37, 3819.
A. G. Chryulu, T. C. McKee, C. M. Ireland *Tetrahedron Lett.* 1989, 30, 4201.
T. F. Molinksy, *Chem. Rev.* 1993, 93, 1825.
J. Kobayashi, J. Cheng, M. R. Walchli, H. Nakamura, Y. Hirata, T. Sasaki, Y. Ohizumi *J. Org. Chem.* 1988, 53, 1800.
J. Kobayashi, M. Tsuda, A. Tanabe, M. Ishibashi, J. F. Cheng, Y. Yamamura, T. Sasaki, *J. Nat. Prod.* 1991, 54, 1634.
J. Kim, E. O. Pordesimo, S. I. Toth, F. J. Schmitz, I. Van Altena, *J. Nat. Prod.* 1993, 56, 1813.
M. Ionescu, I. Mester, *Rev. Roum. Chim.,* 1969, 14, 789.
T. W. Greene, P. G. M. Wuts, "Protecting Groups in Organic Synthesis", John Wiley & Sons, 1991.
R. J. Bergeron, P. F. Cavanaugh, Jr., S. J. Kline, R. G. Hughes, Jr., G. T. Elliot, C. W. Porter, *Biochem. Bioph. Res. Comm.* 1984, 121, 848.
A. C. Schroeder, R. G. Hughes, Jr., A. Bloch, *J. Med. Chem.* 1981, 24, 1078.

What is claimed is:

1. A compound of formula (I):

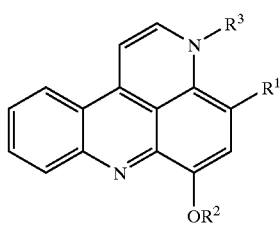

(I)

wherein:
R$^1$ represents a hydrogen atom, an alkyl group having from 1 to 6 carbon atoms, a hydroxy group, an alkoxy group having from 1 to 6 carbon atoms, a halogen atom, a nitro group, an amino group, a monoalkylamino group wherein the alkyl moiety has from 1 to 6 carbon atoms, a dialklylamino group wherein each alkyl moiety may be the same or different and each has from 1 to 6 carbon atoms, a monoalkoxyamino group wherein the alkoxy moiety has from 1 to 6 carbon atoms, a dialkoxyamino group wherein each alkoxy moiety may be the same or different and each has from 1 to 6 carbon atoms, an alkanoylamino group having from 1 to 20 carbon atoms or an alkanesulfonylamino group having from 1 to 6 carbon atoms;
R$^2$ represents a hydrogen atom or an alkyl group having from 1 to 6 carbon atoms; and
R$^3$ represents a hydrogen atom, an alkyl group having from 1 to 6 carbon atoms or an alkoxy group having from 1 to 6 carbon atoms;
and pharmaceutically acceptable salts thereof.

2. A compound according to claim 1, in which R$^1$ represents a hydrogen atom, an alkyl group having from 1 to 6 carbon atoms, a hydroxy group, an alkoxy group having from 1 to 6 carbon atoms, a nitro group, an amino group, a monoalkylamino group wherein the alkyl moiety has from 1 to 6 carbon atoms, a dialkylamino group wherein each alkyl moiety may be the same or different and each has from 1 to 6 carbon atoms, an alkanoylamino group having from 1 to 20 carbon atoms or an alkanesulfonylamino group having from 1 to 6 carbon atoms.

3. A compound according to claim 1, in which R$^1$ represents a hydrogen atom, an alkyl group having from 1 to 4 carbon atoms, a nitro group, an amino group, a monoalkylamino group wherein the alkyl moiety has from 1 to 4 carbon atoms, a dialkylamino group wherein each alkyl moiety may be the same or different and each has from 1 to 4 carbon atoms, an alkanoylamino group having from 1 to 6 carbon atoms or an alkanesulfonylamino group having from 1 to 4 carbon atoms.

4. A compound according to claim 1, in which R$^1$ represents a hydrogen atom, a nitro group, an amino group or an alkanoylamino group having from 1 to 4 carbon atoms.

5. A compound according to claim 1, in which R$^2$ represents a hydrogen atom or an alkyl group having from 1 to 4 carbon atoms.

6. A compound according to claim 1, in which R$^2$ represents a hydrogen atom or a methyl group.

7. A compound according to claim 1, in which R$^3$ represents a hydrogen atom or an alkyl group having from 1 to 4 carbon atoms.

8. A compound according to claim 1, in which R$^3$ represents a hydrogen atom or a methyl group.

9. A compound according to claim 1, in which R$^3$ represents a hydrogen atom.

10. A compound according to claim 1, in which:
R$^1$ represents a hydrogen atom, an alkyl group having from 1 to 6 carbon atoms, a hydroxy group, an alkoxy group having from 1 to 6 carbon atoms, a nitro group, an amino group, a monoalkylamino group wherein the alkyl moiety has from 1 to 6 carbon atoms, a dialkylamino group wherein each alkyl moiety may be the same or different and each has from 1 to 6 carbon atoms, an alkanoylamino group having from 1 to 20 carbon atoms or an alkanesulfonylamino group having from 1 to 6 carbon atoms;
R$^2$ represents a hydrogen atom or an alkyl group having from 1 to 4 carbon atoms; and
R$^3$ represents a hydrogen atom or an alkyl group having from 1 to 4 carbon atoms.

11. A compound according to claim 1, in which:
R$^1$ represents a hydrogen atom, an alkyl group having from 1 to 4 carbon atoms, an nitro group, an amino group, a monoalkylamino group wherein the alkyl moiety has from 1 to 4 carbon atoms, a dialkylamino group wherein each alkyl moiety may be the same or different and each has from 1 to 4 carbon atoms, an alkanoylamino group having from 1 to 6 carbon atoms or an alkanesulfonylamino group having from 1 to 4 carbon atoms;
R$^2$ represents a hydrogen atom or a methyl group; and
R$^3$ represents a hydrogen atom or a methyl group.

12. A compound according to claim 1, in which:
R$^1$ represents a hydrogen atom, a nitro group, an amino group or an alkanoylamino group having from 1 to 4 carbon atoms;
R$^2$ represents a hydrogen atom or a methyl group; and
R$^3$ represents a hydrogen atom.

13. A compound according to claim 1, selected from the following:
3H-6-methoxypyrido[2,3,4-kl]acridine;
3H-6-hydroxypyrido[2,3,4-kl]acridine;
3H-6-methoxy-4-nitropyrido[2,3,4-kl]acridine;
3H-4-acetylamino-6-methoxypyrido[2,3,4-kl]acridine;
and pharmaceutically acceptable salts thereof.

14. A pharmaceutical composition containing as an active ingredient a compound of formula (I) as defined in any one of claims 1 to 13 or a pharmaceutically acceptable salt thereof together with a pharmaceutically acceptable carrier or diluent.

15. A method for treating a mammal affected by a malignant tumour, which comprises administering to a mammal in need of such treatment a therapeutically effective amount of a compound of formula (I), a pharmaceutically acceptable salt thereof as defined in any one of claims 1 to 13 or a pharmaceutical composition thereof as defined in claim 14.

16. A method for preparing a compound of formula (I) as defined in any one of claims 1 to 13 or a pharmaceutically acceptable salt thereof, comprising the following steps:

reacting a compound of formula (II):

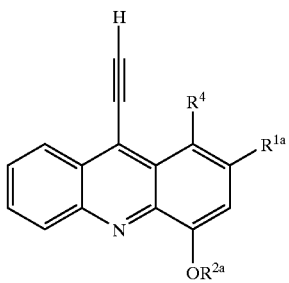

(II)

wherein:
- $R^{1a}$ represents any of the groups represented by $R^1$, and any group wherein OH and NH groups (if any) are protected;
- $R^{2a}$ represents an alkyl group having from 1 to 6 carbon atoms or a hydroxy-protecting group; and
- $R^4$ represents a hydrogen atom, an alkyl group having from 1 to 6 carbon atoms or an alkoxy group having from 1 to 6 carbon atoms;

with a compound of formula (III):

(III)

wherein M represents a Group 1 metal ion, a Group 2 metal ion or a tetraalkylammonium ion (in which each alkyl group may be the same or different and each has from 1 to 20 carbon atoms), and n stands for an integer equal to the positive valency of M;

to give a compound of formula (Ia):

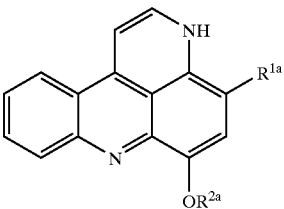

(Ia)

in which $R^{1a}$ and $R^{2a}$ are as defined above;

and, if necessary, removing protecting groups;

and, if necessary, any of the following steps (i) to (v):
(i) converting the group $R^{1a}$ to any of the other groups represented by $R^1$;
(ii) where $R^2$ represents an alkyl group, alkylating the product;
(iii) where $R^3$ represents an alkyl group, alkylating the product;
(iv) where $R^3$ represents an alkoxy group, alkoxylating the product;
(v) salifying the product to give a pharmaceutically acceptable salt of the compound of formula (I).

* * * * *